United States Patent [19]
Paul et al.

[11] Patent Number: 5,628,776
[45] Date of Patent: May 13, 1997

[54] IMPLANTABLE LEAD WITH WARNING SYSTEM

[75] Inventors: Patrick J. Paul; David Prutchi, both of Lake Jackson, Tex.

[73] Assignee: Intermedics, Inc., Angleton, Tex.

[21] Appl. No.: 426,949

[22] Filed: Apr. 21, 1995

[51] Int. Cl.$^6$ .................................................. A61N 1/04
[52] U.S. Cl. .................................................. 607/119
[58] Field of Search ........................... 128/908; 607/2, 607/5, 9, 27, 29, 34, 63, 116, 119, 122, 129

[56] References Cited

U.S. PATENT DOCUMENTS

| | | | |
|---|---|---|---|
| 3,783,877 | 1/1974 | Bowers | 607/34 |
| 4,038,990 | 8/1977 | Thompson | 607/9 |
| 4,140,131 | 2/1979 | Dutcher et al. | 128/419 PT |
| 5,076,272 | 12/1991 | Ferek-Petric | 128/419 PG |
| 5,325,870 | 7/1994 | Kroll et al. | 607/122 |

FOREIGN PATENT DOCUMENTS 4213993  12/1992  Germany ............. A61N 1/08

*Primary Examiner*—William E. Kamm
*Attorney, Agent, or Firm*—John R. Merkling

[57] ABSTRACT

A cardiac simulation system including a patient warning apparatus. The cardiac stimulator is an implantable pacemaker or defibrillator or combination which can be programmed to automatically alter the voltage of its output stimulus, in particular, to increase the voltage of the output stimulus whenever a condition exists requiring patient notification or warning. A specialized auxiliary lead with a shunt circuit can be connected to a standard socket of a cardiac stimulator header and a standard lead, such as a cardiac pacemaker lead, can then be connected to the auxiliary lead. The auxiliary lead allows a stimulation electrode to be implanted near excitable tissue in a secure fashion to assure stimulation of tissue. The auxiliary lead includes an apparatus for shunting electrical current from the standard stimulation electrode implanted in or near the patient's heart to the auxiliary electrode in the presence of a stimulation pulse with a voltage at or above a preselected level.

18 Claims, 4 Drawing Sheets

IMPLANTABLE LEAD WITH WARNING SYSTEM

FIELD OF OUR INVENTION

Our invention relates to cardiac pacemakers and other cardiac stimulators which monitor the operation of the heart and stimulate the heart tissue as required to maintain the proper operation of the heart, including implantable cardioverters and defibrillators. In particular, our invention relates to an implantable cardiac stimulating system with the capability of alerting or warning a patient of certain conditions or situations, including, without limitation, battery depletion, lead malfunction, or the eminent delivery of therapy.

BACKGROUND OF OUR INVENTION

It has long been known that the heart muscle provides its pumping function in response to electrical events which occur within the atrium and ventricle of the heart. Conductive tissue connects the atrium and the ventricle and provides a path for electrical signals between the two areas. In a normal heart, a natural atrial event spontaneously occurs in the atrium and a corresponding ventricular event occurs later in the ventricle. Synchronized electrical events occurring naturally in the atrium and ventricle cause the heart muscle to rhythmically expand and contract and thereby pump blood throughout the body.

In a diseased heart, atrial and ventricular events may not naturally occur in the required synchronized manner and the pumping action of the heart is therefore irregular and ineffective to provide the required circulation of blood. The required synchronized activity of such diseased hearts can be maintained by any implanted cardiac pacemaker which applies synchronized stimulating pulses to either the atrium or ventricle or both.

A diseased heart may also beat unusually quickly, a condition known as tachycardia, or may lapse into a rapid, disorganized quivering known as fibrillation. The former condition is undesirable, a latter condition may be fatal. To correct these conditions, implantable cardioverters and defibrillators have been proposed. Like the related cardiac pacemaker, these devices monitor the electrical condition of the heart and provide a corrective electrical therapy to correct the improper heart function. The three functions of pacing, cardioverting and defibrillating, or any of them, may be incorporated into a single device, generically, an implantable cardiac stimulator.

Cardiac stimulators are battery powered and, consequently, have a finite life before battery depletion may be expected. In addition to the battery, other components of the cardiac stimulation system may fail, such as leads, electrodes, or other system components. As an example of another type of change, the sensitivity of a patient's heart to electrical stimulation may change over time, altering the so-called threshold level for electrical stimulation. Such change of condition requires adaptation of the therapy delivered by the implantable cardiac stimulator, either automatically or by intervention by the attending physician. In any of these situations, or others, it may be deemed desirable to alert the patient to a changed condition so that action may be taken. For example, a pacemaker may detect the approaching end of life of its battery, in a known manner. It is desirable to alert the patient to this condition. Moreover, in the case of implantable defibrillators, delivery of therapy can be traumatic. It is sometimes deemed important to alert the patient to the prospect to eminent delivery of therapy.

Cardiac stimulators which alert or warn the patient of such conditions are known in the art. For example, such a device is described by Dutcher, et al. in U.S. Pat. No. 4,140,131. In the device described by Dutcher, et al., a device-controlled switch is activated to enable a specialized electrode adjacent the pacemaker to stimulate the patient's muscles to twitch. The nature of the electrode is not described in detail, but Ferek-Petrick, in U.S. Pat. No. 5,076,272, described the electrode of Dutcher, et al., as an auxiliary electrode surrounded by the indifferent electrode and fixed on the pacemaker can. In contrast, Ferek-Petrick, in U.S. Pat. No. 5,076,272, describes a cardiac stimulator with patient warning with an electrode affixed to the header of the stimulator.

We have found, however, that a warning electrode mounted directly on the casing or can of a cardiac stimulator or to the header is frequently ineffective in providing the necessary stimulus to the voluntary muscles of the patient to produce an effective twitch. Moreover, specialized pacemakers are necessary to employ the inventions described heretofore.

It is an object of our invention, therefore, to provide means whereby a standard pacemaker, capable of being programmed, may be modified to include a patient warning apparatus. It is a further object of our invention to provide a remote auxiliary electrode for the purpose of providing patient warning signals by stimulating excitable tissue of the patient, for example, nerve ends or voluntary muscles. It is a further object of our invention to provide for an effective implantable cardiac stimulation system with a reliable patient warning apparatus.

SUMMARY OF OUR INVENTION

In view of the foregoing, we have invented a cardiac simulation system including a patient warning apparatus. In our preferred embodiment, the cardiac stimulator is an implantable pacemaker or defibrillator or combination which can be programmed to automatically alter the peak voltage of its output stimulus, in particular, to increase the peak voltage of the output stimulus whenever a condition exists requiring patient notification or warning. Our invention includes a specialized auxiliary lead with a shunt circuit. The auxiliary lead can be connected to a standard socket of a cardiac stimulator header and a standard lead, such as a cardiac pacemaker lead, can then be connected to the auxiliary lead. The auxiliary lead allows a stimulation electrode to be implanted near excitable tissue in a secure fashion to assure stimulation of tissue. The auxiliary lead includes an apparatus for shunting electrical current from the standard stimulation electrode implanted in or near the patient's heart to the auxiliary electrode in the presence of a stimulation pulse with a voltage at or above a preselected level. With the foregoing in mind, we will now describe the preferred embodiment of our invention with respect to the accompanying drawings.

DETAILED DESCRIPTION OF OUR PREFERRED EMBODIMENT

Figure 1:
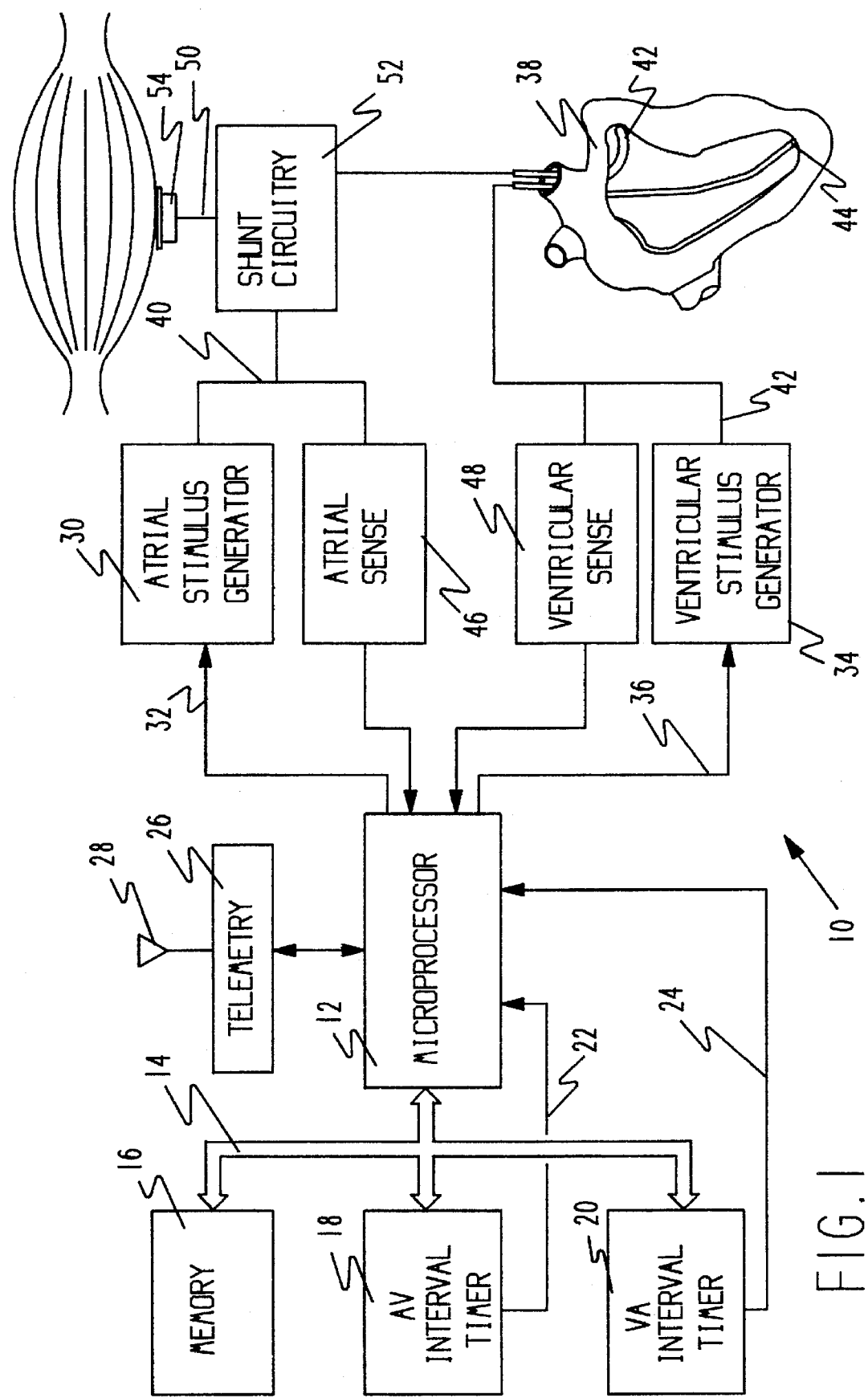
FIG. 1 is a block diagram of a cardiac stimulation system according to our invention, including an auxiliary lead and auxiliary electrode.

FIG. 1 is a block diagram illustrating a cardiac stimulator, generally designated 10, according to our invention. We have illustrated our invention in connection with a dual chamber pacemaker, but our invention is equally applicable with other implantable cardiac stimulators such as cardioverters and defibrillators, as are known in the art.

A microprocessor 12 preferably provides control and computational facilities. It will be appreciated that other forms of circuitry, such as analog or discrete digital circuitry, can be used in place of the microprocessor 12. However, a microprocessor is preferred for its miniature sized and flexibility, both of which are of critical importance for the implantable systems in which it is envisioned our invention will find use. More particularly, a cardiac stimulator having a microprocessor can usually be re-programmed to utilize our invention without additional structural changes, with the exception of the provision of the auxiliary lead, to be described hereafter. A particularly energy efficient microprocessor which is designed specifically for use in pacemakers is fully described in Gordon, et al, U.S. Pat. No. 4,404,972, which is assigned to the assignee of our invention. The disclosure thereof is incorporated herein by reference.

The microprocessor 12 has input/output ports connected in a conventional matter via a bi-directional bus 14 to memory 16, an AV interval timer 18, and a VA pacing interval timer 20. In addition, the AV interval timer 18 and VA interval timer 20 each has an output connected individually to a corresponding input port of the microprocessor 12 by lines 22 and 24 respectively. Memory 16 preferably includes both ROM and RAM. The microprocessor 12 may also contain additional ROM and RAM as described in Gordon, et al., above. Generally, the pacemaker operating routine is stored in ROM or EPROM memory. RAM stores various programmable parameters and variables used in conjunction with the pacemaker operation.

The AV and VA interval timers 18, 20, may be external to the microprocessor 12, as illustrated, or internal thereto, as described in Gordon, et al., above. The timers 18, 20 are conventional up or down counters of a type initially loaded with count value and count up to or down from the value and output a roll-over bit on completing the programmed count.

The microprocessor 12 preferably has an input/output port connected to a telemetry interface 26. The implanted cardiac stimulator 10 is thus able to receive pacing, rate control, or other parameters from an external programmer through an antenna 28 and to send data to an external receiver if desired. Many suitable telemetry systems are known to those skilled in the art. One such system and coding arrangement is described in Calfee, et al. U.S. Pat. No. 4,539,992 which is also assigned to the assignee of our invention. That description is incorporated therein by reference.

Microprocessor output ports are connected to the input of an atrial stimulus pulse generator 30 by a control line 32. Similarly a ventricular stimulus generator 34 is connected to the microprocessor by a control line 36. The microprocessor 12 transmits pulse parameter data, such as pulse amplitude and width, as well as enable/disable and pulse initiation codes to the atrial and ventricular stimulus generators 30, 34 along their control lines 32, 36 respectively. The atrial stimulus generator 30 is connected to the heart 38 by a first lead 40 with an electrode 42. Similarly, the ventricular stimulus generator 34 is connected to the heart 38 by a second lead 42 with a corresponding electrode 44. The electrical condition of the heart must also be sensed and that condition must be transmitted to the microprocessor 12. For this purpose, an atrial sense amplifier 46 is connected between the lead 40 and the microprocessor 12. Similarly, a ventricular sense amplifier 28 is connected between the lead 42 and the microprocessor 12. The atrial ventricular sense amplifiers 46, 48 detect occurrences of P waves and R waves respectively. The cardiac stimulator 10 of our invention is also provided with at least one auxiliary lead 50. In the illustrated embodiment the auxiliary lead 50 is connected to the atrial or first lead 40 but it could equally well be connected to the ventricular lead 42. Also, two auxiliary leads could be provided, one for each channel connected to the heart. The auxiliary lead 50 comprises shunt circuitry 52 which allows a relatively high voltage stimulating pulse to be passed to an electrode 54 attached to excitable tissue 51 of the patient, rather than or in addition to the electrode 42. The excitable tissue could be voluntary muscle, a nerve ending, or other tissue capable of a perceptible physiologic reaction in response to stimulation.

The auxiliary lead 50 may be made unitary with the lead 40 connected to the heart 38. Our preferred embodiment includes an additional lead as illustrated in perspective view in FIG. 2. A first optional auxiliary lead is illustrated as 56 in FIG. 2. The first optional lead comprises a first lead segment 58 containing a coiled conductor within a silicone or polyethylene sheath. A connector or plug 60, preferably a VS-1 type pacemaker connector, is provided at a distal end thereof for insertion into the header of a pacemaker, in the same fashion as an ordinary lead. The auxiliary electrode further comprises a chamber 62 containing shunt circuitry 52 to be described more fully hereafter and a socket 64 for receiving a male plug of a standard cardiac pacing lead. In our preferred embodiment, the socket 64 has a configuration conforming to the well-known VS-1 standard, adopted heretofore by the pacemaker industry generally. The socket 64 and the plug 60 are in electrical communication through the mentioned coil. At the chamber 62, tabs 66, 68 are provided for stitching of the chamber to a selected location in the patient's body, thus securing the auxiliary lead 56 against body motions. A second lead segment 70 connects the chamber 62 with an electrode 72. The lead segment 70 preferably comprises a tri-filar coiled electrical conductor encased in silicone or polyethylene. The conductor (not shown) connects the chamber 64 electrically with the electrode 72. In our illustrated and preferred embodiment, the electrode 72 is similar in configuration to an endocardial electrode. Such an electrode frequently has a flange 74 surrounding a helix 76. The helix 76 may be screwed into selected excitable tissue, such as voluntary muscle, and the flange 74 can then be stitched into place to further secure the electrode. The electrode 72 is in electrical communication through the conductor and the shunt circuitry 52 with the plug 60 and the socket 64.

Figure 2:
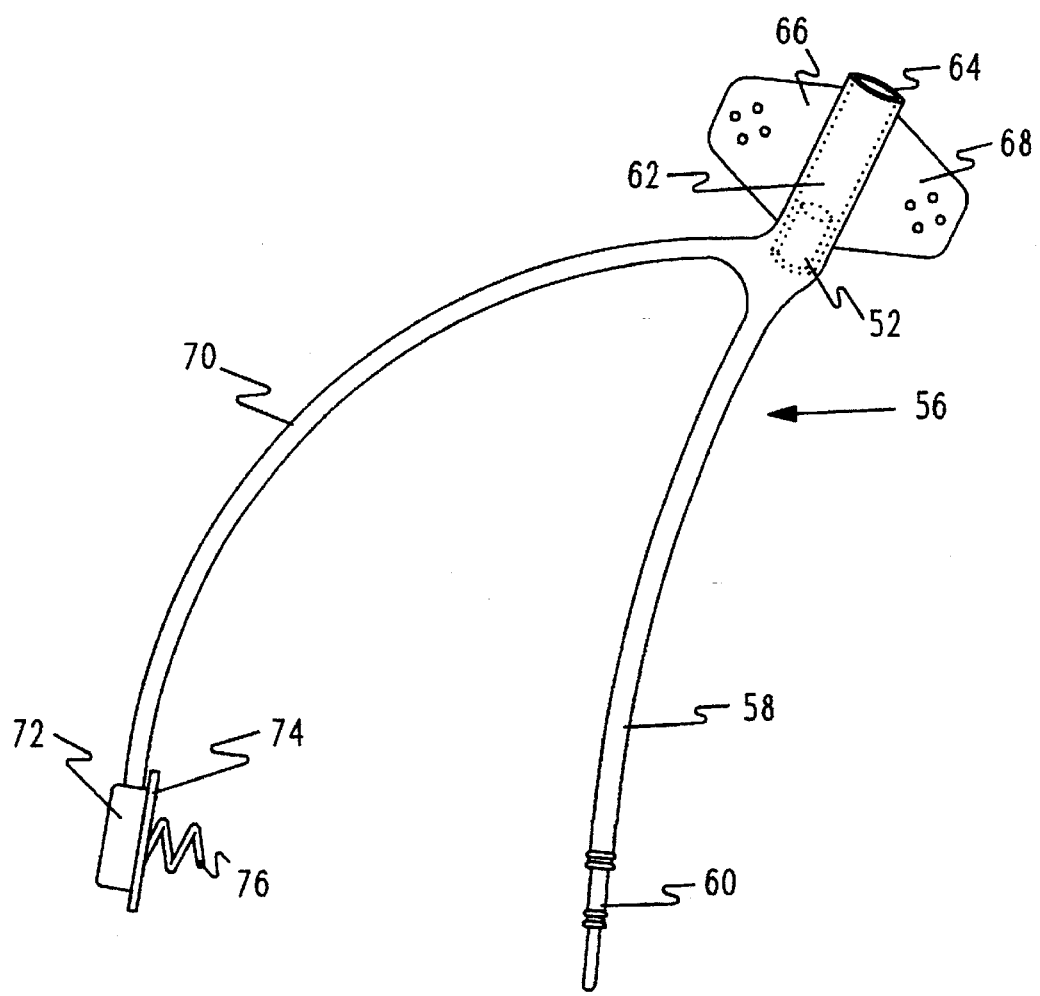
FIG. 2 is a perspective drawing of an auxiliary lead according to our invention.
Figure 3:
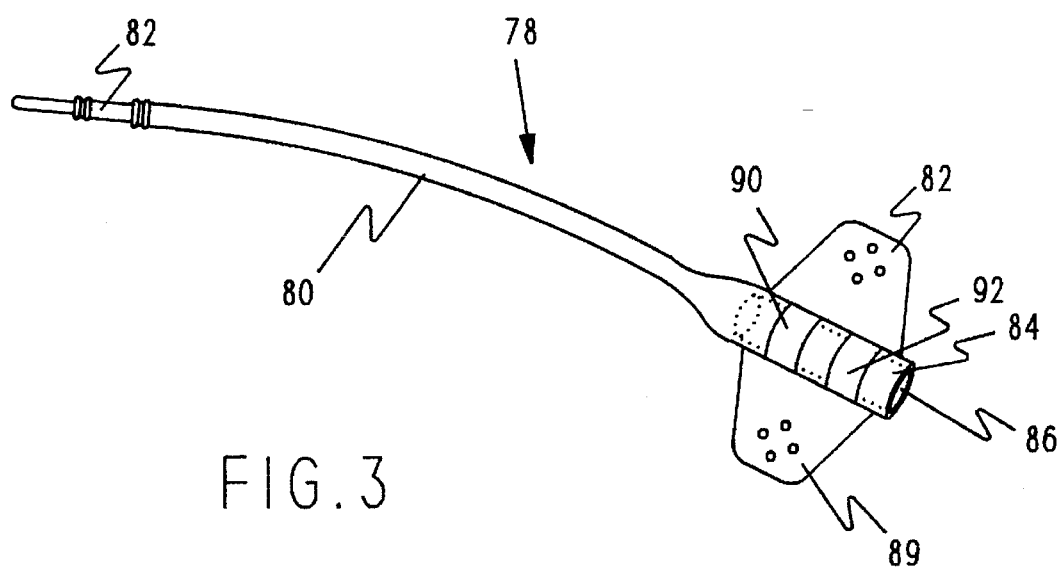
FIG. 3 is a perspective view of an alternative embodiment of an auxiliary lead according to our invention.

An alternative embodiment is illustrated in FIG. 3. In FIG. 3, a second auxiliary lead 78 is illustrated. The second auxiliary lead 78 comprises a lead segment 80 having a tri-filar coil conductor with silicone or polyethylene sheathing. The segment 80 connects a male plug 82 of the VS-1 type to a chamber 84 having a socket 86, also of the VS-1 type in the female configuration. This embodiment also has tabs 88 and 90 which permit the chamber 84 to be secured adjacent excitable tissue. In contrast to the embodiment of FIG. 2, however, the segment of auxiliary lead 78 has voluntary muscle stimulating electrodes 90, 92 on the chamber 84 itself. Within the chamber 84, shunt circuitry 52 (not shown in FIG. 3) connects the conductor to the socket 86.

To utilize our invention, a programmable pacemaker is reprogrammed to produce a high-voltage stimulation whenever it is desired to notify the patient of a condition. In prior art devices such as that disclosed in U.S. Pat. No. 5,076,272, various conditions requiring patient notification or warning have heretofore been identified. In general, a muscle stimulating electrode has been provided, and a switch has been utilized to redirect a stimulating pulse from the heart to a voluntary muscle. In our invention, no such separately controllable switch is required. Rather, the magnitude of the programmed peak output voltage determines the path of the current.

Figure 7:
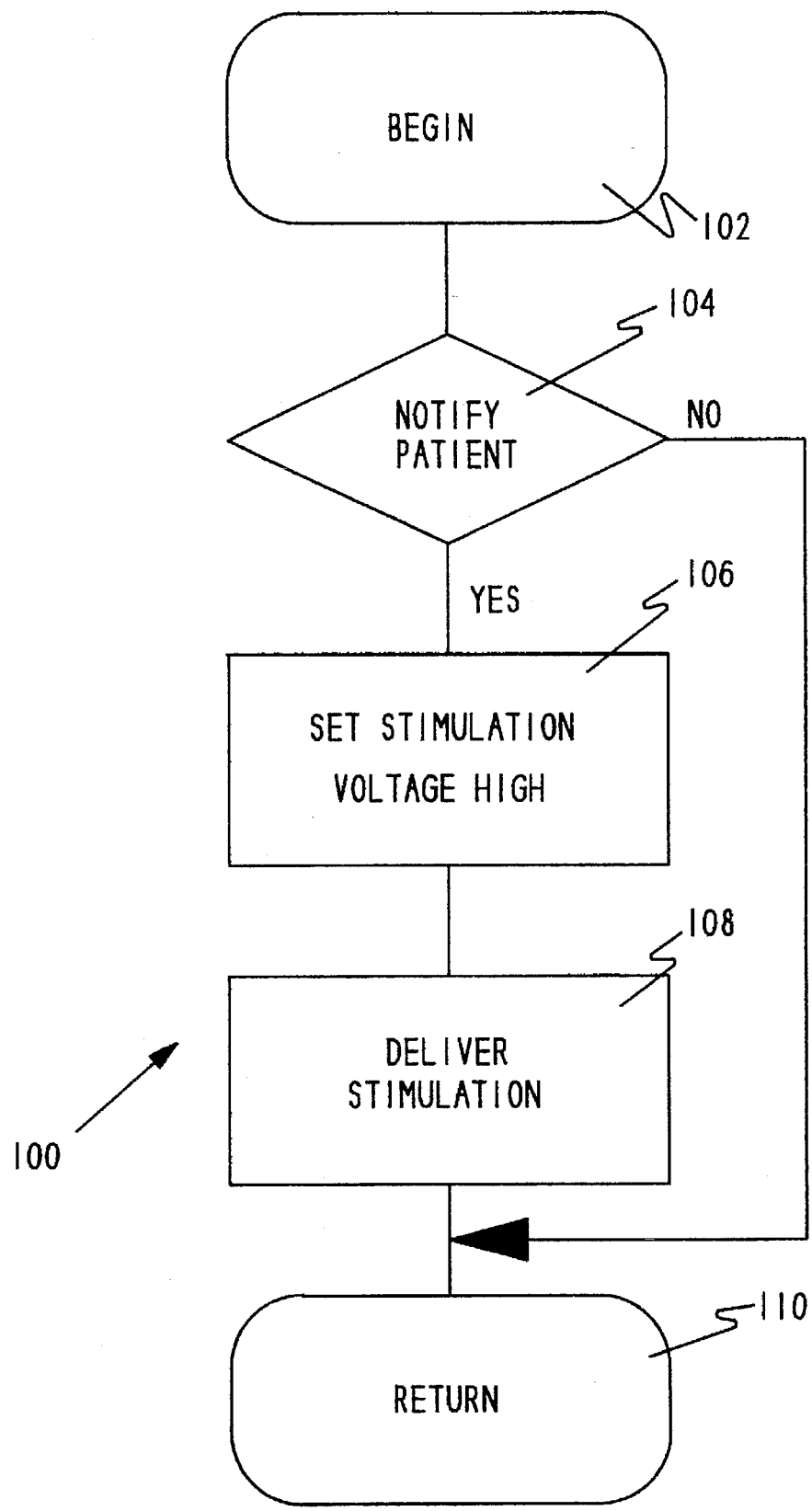
FIG. 7 is a flow chart for a program to be implemented in the cardiac stimulator of FIG. 1.

In the pacemaker, a notification program, such as that indicated at 100 in FIG. 7, is needed. In addition to other standard pacemaker or cardioverter programming, a program segment illustrated at 100 would begin 102 and pass to a test 104 to enquiring whether the patient should be notified or not. This program sequence could be a single test controlled by a flag, or it might involve multiple tests for different conditions recognized by pacemaker programming and identified in an appropriate manner, such as by setting a flag. These tests could include battery voltage level, presence of inappropriate tachycardia, or eminence of an impending defibrillation shock or other therapy, among other indicators. If there is no condition existing justifying notification or warning of the patient, no further action need be taken in this segment of the microprocessor programming and the program control can branch around the next steps. If it is desired, however, to notify the patient, the microprocessor would adjust the output voltage of the relevant stimulus generator to output impulse at a voltage above a predetermined level. With the voltage set high, the pacemaker would then deliver either ordinary or specialized sequence of paces 108 through the ordinary output channel of the pacemaker. However, because of the existence of a shunt circuit 52 between the cardiac electrode 42 and the auxiliary electrode 54, a large portion of the high voltage stimulation would be redirected away from the heart to the excitable tissue, for example, to a voluntary muscle. After delivery of the relevant stimulation for a preselected period, program control would return 110 to additional standard stimulator programming.

Figure 4:
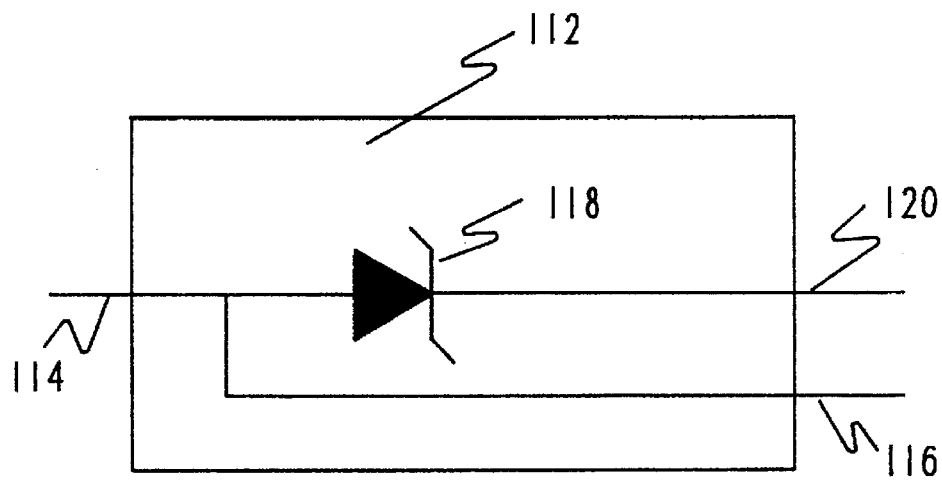
FIG. 4 is a schematic diagram of a first embodiment of a shunt circuitry according to our invention.
Figure 5:
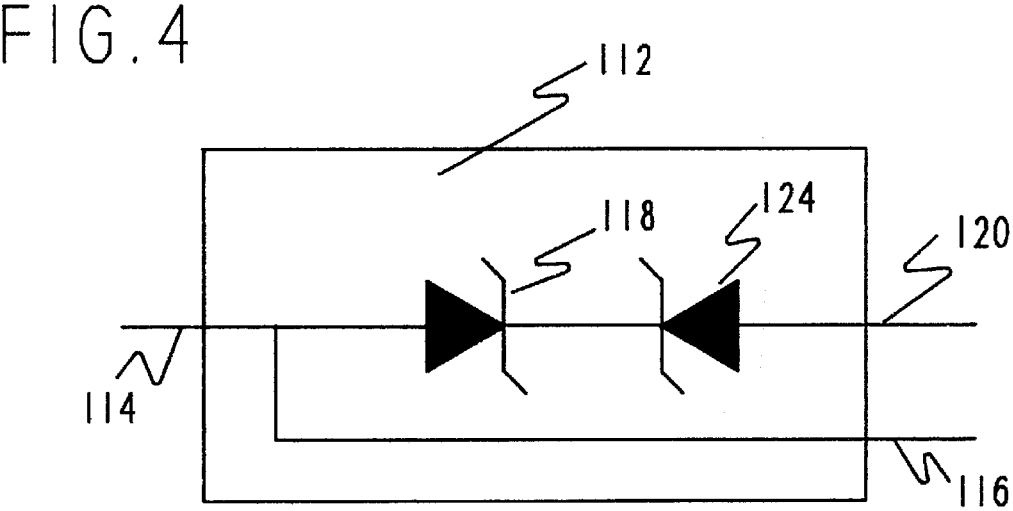
FIG. 5 is a second embodiment of shunt circuitry according to our invention.
Figure 6:
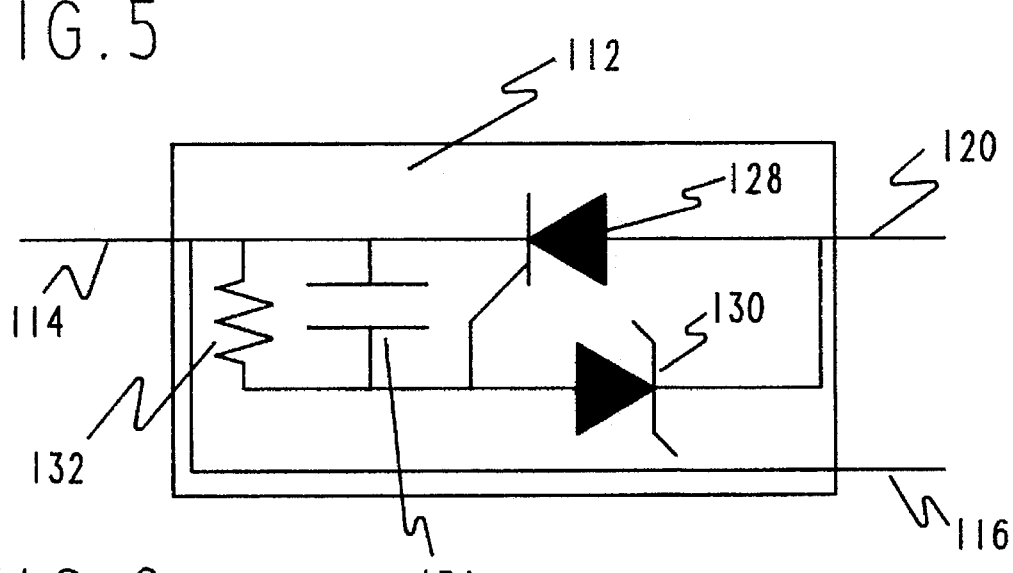
FIG. 6 is a third embodiment of shunt circuitry according to our invention.

Three embodiments of a shunt circuit sensitive to output voltage levels are illustrated in FIGS. 4, 5 and 6. In FIG. 4, a first embodiment 112 of the shunt circuit comprises an input line 114 connected directly to an output 116 for the cardiac stimulation electrode 42 and to a zener diode 118. The diode 118 in turn is connected to the auxiliary electrode 54 on line 120. The break-down voltage of this zener diode is chosen to be above a voltage level necessary for stimulating the heart. The break-down voltage must, however, also be below the maximum output voltage available to the pacemaker. So long as the output voltage of the pacemaker remains below the break-down voltage of the zener diode, all current would be directed to the cardiac electrode and would be used to stimulate the heart. Whenever patient notification is needed, on the other hand, the output voltage would be increased by the microprocessor to a level in excess of the break-down voltage of the zener diode. At that point, the zener diode 118 would become conductive, and a portion of the stimulating pulse would be passed to the auxiliary electrode, causing the voluntary muscle to which it was attached to twitch.

A second improved embodiment 122 is illustrated in FIG. 5 it has all of the elements of the first embodiment 112 of FIG. 4 and also has a reversed second zener diode 124.

A third embodiment 126 of the shunt circuitry is illustrated in FIG. 6. In this, our most preferred embodiment, a semiconductor controlled rectifier or SCR 128, or other suitable solid state device for switching means, is tripped by a zener diode 130 whenever the pacing pulse amplitude exceeds the threshold voltage of the diode 130. Current flow through the diode 130 operates to open the SCR 128 to current flow. Because of the biasing resistor 132 and capacitor 134, the SCR 128 then remains open for a brief period of time dependent on the component values, providing a low impedance path to the lead 120. This implementation has the advantage that the pulse amplitude delivered to the voluntary muscle is higher than that possible through the use of a single zener diode or back-to-back zener diodes as illustrated in FIGS. 4 and 5. The resistor 132 reduces the sensitivity of the SCR to the current passing through the zener diode, even when operating at its threshold voltage. Careful selection of the operating parameters of the SCR 128 and zener diode 130 would reduce the need for the resistor 132. In addition, a small-value capacitor 134 may be needed to filter voltage transients that could cause the shunt circuitry to trigger erroneously.

Although we prefer to mount the shunt circuitry in a separate auxiliary lead as described and illustrated in FIGS. 2 and 3, it would be possible to place the shunt circuitry within the pacemaker itself, particularly in the header of the pacemaker. However, the separate auxiliary lead has the additional advantage that existing, programmable cardiac stimulators can be reprogrammed to include increasing pulse output voltage at appropriate times, and would nevertheless be useable.

Our invention may be embodied in other specific forms without departing from the spirit or essential characteristics thereof. Present embodiment is therefore considered in all respects to be illustrative and not restrictive, the scope of our invention being indicated by the appended claims whether by the foregoing description and all changes which come within the meaning and range of equivalency of the claims are therefore intended to be embraced therein.

We claim as our invention:

1. An auxiliary lead for use with a cardiac stimulation device, comprising a plug for electrically connecting said auxiliary lead to said cardiac stimulation device, a socket for electrically connecting a cardiac stimulation lead to said auxiliary lead, a conductor electrically connecting said plug with said socket, at least one electrode for implantation near an excitable tissue of a patient, and means responsive to a predetermined voltage on said conductor for directing at least part of said output pulse into said excitable tissue electrode, producing a physiologic reaction in said excitable tissue of said patient.

2. The auxiliary lead according to claim 1 wherein said voltage responsive means comprise at least one zener diode.

3. The auxiliary lead according to claim 2 wherein said voltage responsive means comprise two zener diodes in series, one of said diodes having an opposite orientation from the other of said diodes.

4. The auxiliary lead according to claim 1 wherein said voltage responsive means comprise switch means and means for closing said switch for a predetermined period of time after a first occurrence of said high level of said output voltage.

5. The auxiliary lead according to claim 4 wherein said switch means comprise a semiconductor controlled rectifier.

6. The auxiliary lead according to claim 5 wherein said means for closing comprise a zener diode triggering said semiconductor controlled rectifier.

7. The auxiliary lead according to claim 6 wherein said means for closing further comprise a capacitor electrically connected between said conductor and said zener diode.

8. The auxiliary lead according to claim 6 wherein said means for closing further comprise a resistor electrically connected between said conductor and said zener diode.

9. The auxiliary lead according to claim 6 wherein said means for closing further comprise a capacitor electrically connected between said conductor and said zener diode.

10. The auxiliary lead according to claim 1 further comprising a lead segment electrically connecting said electrode to said plug and socket, said lead segment being effective to space said electrode away from said plug and said socket.

11. The auxiliary lead according to claim 10 wherein said voltage responsive means comprise at least one zener diode.

12. The auxiliary lead according to claim 11 wherein said voltage responsive means comprise two zener diodes in series, one of said diodes having an opposite orientation from the other of said diodes.

13. The auxiliary lead according to claim 10 wherein said voltage responsive means comprise switch means and means for closing said switch for a predetermined period of time after a first occurrence of said voltage high level of said output voltage.

14. The auxiliary lead according to claim 13 wherein said switch means comprise a semiconductor controlled rectifier.

15. The auxiliary lead according to claim 14 wherein said means for closing comprise a zener diode triggering said semiconductor controlled rectifier.

16. The auxiliary lead according to claim 15 wherein said means for closing further comprise a capacitor electrically connected between said conductor and said zener diode.

17. The auxiliary lead according to claim 15 wherein said means for closing further comprise a resistor electrically connected between said conductor and said zener diode.

18. The auxiliary lead according to claim 17 wherein said means for closing further comprise a capacitor electrically connected between said conductor and said zener diode.

* * * * *